United States Patent
Kadayam Viswanathan et al.

(10) Patent No.: US 10,345,478 B2
(45) Date of Patent: Jul. 9, 2019

(54) IDENTIFYING AND REMOVING ARTIFACTS FROM MULTI-DIMENSIONAL DISTRIBUTION FUNCTIONS

(71) Applicant: Schlumberger Technology Corporation, Sugar Land, TX (US)

(72) Inventors: Ravinath Kausik Kadayam Viswanathan, Boston, MA (US); Martin D. Hurlimann, Newton, MA (US); Colm Ryan, Cambridge, MA (US); Frank P. Shray, Littleton, CO (US); Yi-Qiao Song, Newton Center, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 737 days.

(21) Appl. No.: 14/727,967

(22) Filed: Jun. 2, 2015

(65) Prior Publication Data

US 2015/0346378 A1 Dec. 3, 2015

Related U.S. Application Data

(60) Provisional application No. 62/006,650, filed on Jun. 2, 2014.

(51) Int. Cl.
*G01V 3/32* (2006.01)
*G01N 24/08* (2006.01)
*G01R 33/44* (2006.01)
*G01R 33/563* (2006.01)

(52) U.S. Cl.
CPC ............. *G01V 3/32* (2013.01); *G01N 24/081* (2013.01); *G01R 33/44* (2013.01); *G01R 33/448* (2013.01); *G01R 33/56341* (2013.01)

(58) Field of Classification Search
CPC ........... G01V 3/32; G01N 24/08; G01R 33/44
See application file for complete search history.

(56) References Cited

U.S. PATENT DOCUMENTS

| | | |
|---|---|---|
| 2003/0178994 A1* | 9/2003 | Hurlimann ........... G01N 24/081 324/303 |
| 2004/0000905 A1* | 1/2004 | Freedman ............ G01N 24/081 324/303 |
| 2004/0027123 A1* | 2/2004 | Heaton ................ G01N 24/081 324/303 |

(Continued)

OTHER PUBLICATIONS

Hürlimann, M. D. et al. The Diffusion-Spin Relaxation Time Distribution Function as an Experimental Probe to Characterize Fluid Mixtures in Porous Media, The Journal of Chemical Physics, 2002, 117(22), pp. 10223-10232.

(Continued)

*Primary Examiner* — Michael J Dalbo
(74) *Attorney, Agent, or Firm* — Michael Dae

(57) ABSTRACT

Systems and methods for generating a multi-dimensional distribution function. First data and second data may be received in response to one or more radiofrequency pulses that are transmitted into a subterranean formation. The first data may include Carr-Purcell-Meiboom-Gill data, and the second data may include diffusion editing data with initial echo spacings longer than subsequent echo spacings. The second data may be inverted. A multi-dimensional distribution function may be determined using the inverted second data.

15 Claims, 6 Drawing Sheets

(56) References Cited

U.S. PATENT DOCUMENTS

| | | | | |
|---|---|---|---|---|
| 2004/0189296 A1* | 9/2004 | Sun | ............... | G01N 24/081 |
| | | | | 324/306 |
| 2008/0024128 A1* | 1/2008 | Song | ............... | G01N 24/081 |
| | | | | 324/307 |
| 2011/0234220 A1* | 9/2011 | Mitchell | ............... | G01N 24/081 |
| | | | | 324/303 |
| 2013/0057277 A1* | 3/2013 | Zielinski | ............... | G01V 3/32 |
| | | | | 324/303 |
| 2013/0162247 A1* | 6/2013 | Hurlimann | ............... | G01N 24/081 |
| | | | | 324/303 |
| 2014/0033815 A1* | 2/2014 | Oraby | ............... | G01V 3/32 |
| | | | | 73/152.05 |

OTHER PUBLICATIONS

Freed, D., "Dependence on Chain Length of NMR Relaxation Times in Mixtures of Alkanes", Journal of Chemical Physics, 2007, 126(17), pp. 1-10.

Hürlimann, M. D. et al., "Hydrocarbon Composition from NMR Diffusion and Relaxation Data", Petrophysics, 2009, vol. 50(2), pp. 116-129.

Heidler, H. et al., "Spin Dynamics Simulations of Multiple Echo Spacing Pulse Sequences in Grossly Inhomogeneous Fields", AIP Conference Proceedings 2008, 1081, pp. 95-98.

Hürlimann, M. D. et al., "Diffusion-Relaxation Distributions Functions of Sedimentary Rocks in Different Saturation States", Magnetic Resonance Imaging, 2003, 21(3-4), pp. 305-310.

\* cited by examiner

IDENTIFYING AND REMOVING ARTIFACTS FROM MULTI-DIMENSIONAL DISTRIBUTION FUNCTIONS

CROSS-REFERENCE TO RELATED APPLICATIONS

This application claims the benefit of related U.S. Provisional Application Ser. No. 62/006,650, filed on Jun. 2, 2014, titled, "Identifying and Removing Artifacts from Multi-Dimensional Distribution Functions," the disclosure of which is incorporated by reference herein in its entirety.

BACKGROUND

1. Technical Field

The present disclosure relates generally to nuclear magnetic resonance (NMR) logging and, more specifically, to techniques for identifying and removing artifacts in multi-dimensional distribution functions.

2. Background Information

This section is intended to introduce the reader to various aspects of art that may be related to various aspects of the subject matter described and/or claimed below. This discussion is believed to be helpful in providing the reader with background information to facilitate a better understanding of the various aspects of the present disclosure. Accordingly, it should be understood that these statements are to be read in this light, not as admissions of prior art.

Logging tools have long been used in wellbores to make, for example, formation evaluation measurements to infer properties of the formations surrounding the borehole and the fluids in the formations. Common logging tools include electromagnetic tools, nuclear tools, acoustic tools, and NMR tools, though various other types of tools for evaluating formation properties are also available.

NMR logging tools are used to measure the properties of nuclear spins in the formation, such as the longitudinal (or spin-lattice) relaxation time (referred to as $T_1$), transverse (or spin-spin) relaxation time (referred to as $T_2$), and a diffusion coefficient (D). Knowledge of these NMR properties can help aid in the determination of basic formation properties such as permeability and porosity, as well as the fluid properties such as fluid type and viscosity. Multi-dimensional NMR techniques may provide quantitative fractions of different fluids (e.g., oil, water, gas) and a better understanding of the diffusion properties of these fluids in the surrounding formation, including the effects of geometry and restricted diffusion. Diffusion relaxation time ($D$-$T_2$) measurements have also shown to reflect hydrocarbon fluid compositions by correlations with their chemistry. It has been observed that in the practical implementation of these NMR techniques in logging tools, unphysical fast diffusion artifacts in the multi-dimensional distribution functions (e.g., 2D D-T2 maps) may occur. These artifacts may make fluid typing and the determination of fluid dynamics more difficult.

SUMMARY

A summary of certain embodiments disclosed herein is set forth below. It should be understood that these aspects are presented merely to provide the reader with a brief summary of certain embodiments and that these aspects are not intended to limit the scope of this disclosure. Indeed, this disclosure may encompass a variety of aspects that may not be set forth in this section.

A method for generating a multi-dimensional distribution function is disclosed. The method may include receiving first data and second data in response to one or more radiofrequency pulses that are transmitted into a subterranean formation. The first data may include Carr-Purcell-Meiboom-Gill data, and the second data may include diffusion editing data with initial echo spacings longer than subsequent echo spacings. The second data may be inverted. A multi-dimensional distribution function may be determined using the inverted second data.

A method for identifying an artifact in a multi-dimensional distribution function is also disclosed. The method may include receiving first data and second data in response to one or more radiofrequency pulses that are transmitted into a subterranean formation. The first data may include Carr-Purcell-Meiboom-Gill data, and the second data may include diffusion editing data with initial echo spacings longer than subsequent echo spacings. A kernel for the second data may be modified by selecting values for $\alpha$ and $\beta$ that cause a sum of $\alpha+\beta$ to be larger than the sum would be under measured conditions. $\alpha$ may represent a relative contribution of a direct echo pathway to the second data, and $\beta$ may represent a relative contribution of a stimulated echo pathway to the second data. The first data and the second data may be inverted using the modified kernel for the second data. A multi-dimensional distribution function may be determined using the inverted first data and the inverted second data.

A computing system for performing one or more of the methods is also disclosed. The computer system may include a processor and a memory system. The memory system may include a computer-readable medium storing instructions thereon that, when executed by the processor, cause the computing system to perform operations. The operations may include receiving first data and second data in response to one or more radiofrequency pulses that are transmitted into a subterranean formation. The first data may include Carr-Purcell-Meiboom-Gill data, and the second data may include diffusion editing data with initial echo spacings longer than subsequent echo spacings. The second data may be inverted. A multi-dimensional distribution function may be determined using the inverted second data.

Again, the brief summary presented above is intended to familiarize the reader with certain aspects and contexts of embodiments of the present disclosure without limitation to the claimed subject matter.

BRIEF DESCRIPTION OF THE DRAWINGS

Other aspects and advantages of the invention will become apparent upon reading the following detailed description and upon reference to the drawings in which.

DETAILED DESCRIPTION

One or more specific embodiments of the present disclosure are described below. These embodiments are merely examples of the presently disclosed techniques. Additionally, in an effort to provide a concise description of these embodiments, all features of an actual implementation may not be described in the specification. It should be appreciated that in the development of any such implementation, as in any engineering or design project, numerous implementation-specific decisions are made to achieve the developers' specific goals, such as compliance with system-related and business-related constraints, which may vary from one implementation to another. Moreover, it should be appreciated that such development efforts may be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The embodiments discussed below are intended to be examples that are illustrative in nature and should not be construed to mean that the specific embodiments described herein are necessarily preferential in nature. Additionally, it should be understood that references to "one embodiment" or "an embodiment" within the present disclosure are not to be interpreted as excluding the existence of additional embodiments that also incorporate the recited features. Further, as used herein, the terms "inner" and "outer"; "up" and "down"; "upper" and "lower"; "upward" and "downward"; "above" and "below"; "inward" and "outward"; and other like terms as used herein refer to relative positions to one another and are not intended to denote a particular direction or spatial orientation. The terms "couple," "coupled," "connect," "connection," "connected," "in connection with," and "connecting" refer to "in direct connection with" or "in connection with via another element or member."

Figure 1:
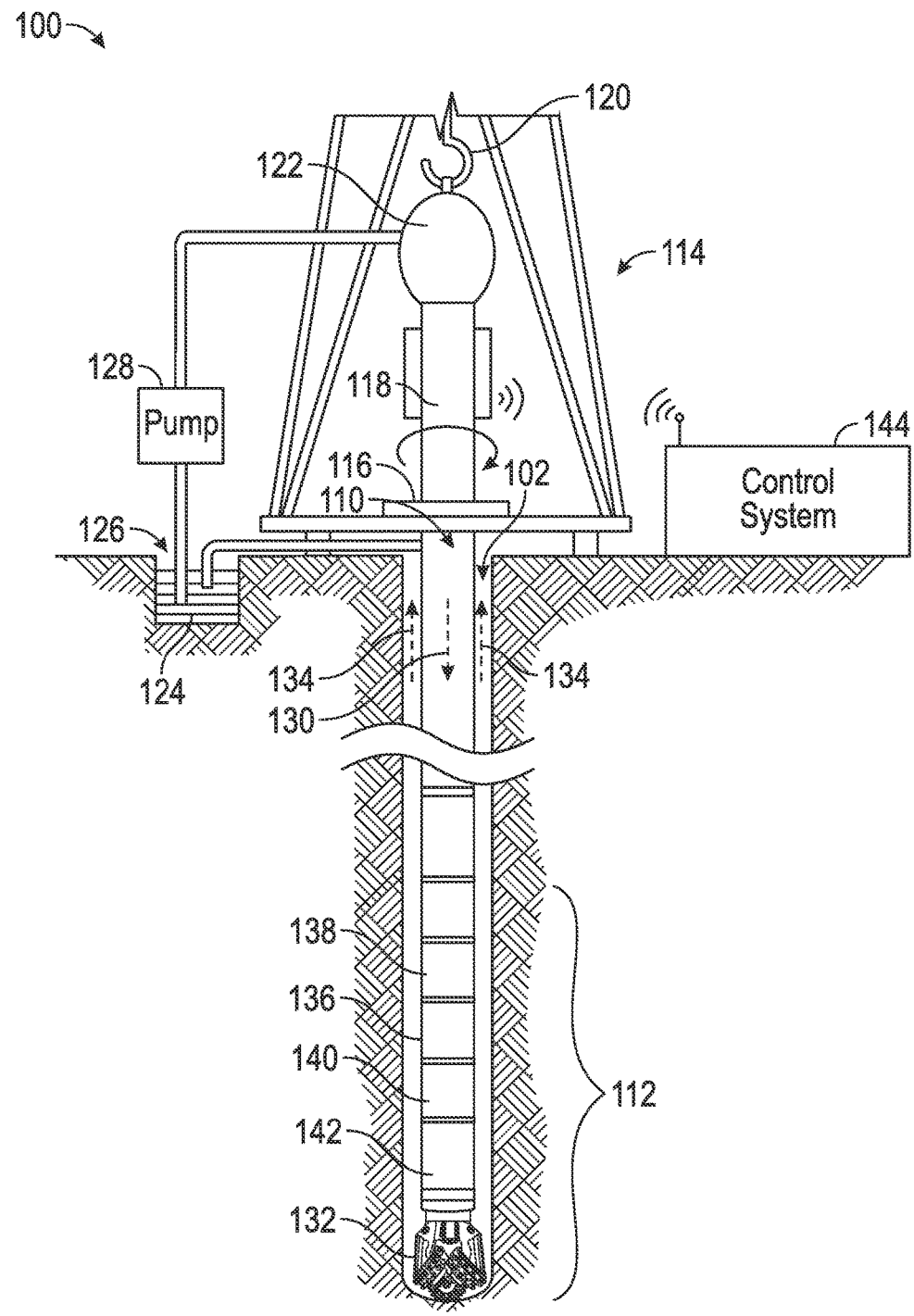
FIG. 1 depicts a schematic side view of an illustrative well site system including a drill string and a bottom hole assembly disposed within a wellbore, according to one or more embodiments disclosed.

FIG. 1 depicts a schematic side view of an illustrative well site system 100 including a drill string 110 and a bottom hole assembly (BHA) 112 disposed within a wellbore 102, according to one or more embodiments disclosed. The well site system 100 may be deployed in either onshore or offshore applications. In this type of system, the wellbore 102 may be formed in subsurface formations by rotary drilling in a manner that is well-known to those skilled in the art. Some embodiments may also use directional drilling.

The drill string 110 may be suspended within the wellbore 102. The well site system 100 may include a platform and derrick assembly 114 positioned over the wellbore 102, with the derrick assembly 114 including a rotary table 116, a kelly 118, a hook 120, and a rotary swivel 122. In a drilling operation, the drill string 110 may be rotated by the rotary table 116, which engages the kelly 118 at the upper end of the drill string 110. The drill string 110 may be suspended from the hook 120, attached to a traveling block (not shown), through the kelly 118 and the rotary swivel 122, which permits rotation of the drill string 110 relative to the hook 120. As is well-known, a top drive system may be used in other embodiments.

Drilling fluid or mud 124 may be stored in a pit 126 formed at the well site. A pump 128 may deliver the drilling fluid 124 to the interior of the drill string 110 via a port in the swivel 122, which causes the drilling fluid 124 to flow downwardly through the drill string 110, as indicated by the directional arrow 130. The drilling fluid exits the drill string 110 via ports in a drill bit 132, and then circulates upwardly through the annulus region between the outside of the drill string 110 and the wall of the wellbore 102, as indicated by the directional arrows 134. In this known manner, the drilling fluid lubricates the drill bit 132 and carries formation cuttings up to the surface as it is returned to the pit 126 for recirculation.

In the illustrated embodiment, the BHA 112 is shown as having a measurement-while-drilling module (MWD) module 136 and multiple logging-while-drilling (LWD) modules 138, 140. As used herein, the term "module" as applied to MWD and LWD devices is understood to mean either a single tool or a suite of multiple tools contained in a single modular device. Additionally, the BHA 112 may include a rotary steerable system (RSS), a motor 142, and the drill bit 132.

The LWD modules 138, 140 may be housed in a drill collar and may include one or more types of logging tools. The LWD modules 138, 140 may be able to measure, process, and store information, as well as communicate with the surface equipment. By way of example, the LWD modules 138, 140 may be or include NMR logging tools that use permanent magnets to create a strong static magnetic polarizing field inside the formation. The hydrogen nuclei of water and hydrocarbons are electrically charged spinning protons that may create a weak magnetic field, similar to bar magnets. When a strong external magnetic field from the logging tool passes through a formation containing fluids, these spinning protons may align themselves like compass needles along the magnetic field. This process, called polarization, may increase exponentially with $T_1$ (longitudinal relaxation time), while the external magnetic field (referred to as the $B_0$ field) is applied.

Multi-dimensional distribution functions (e.g., two-dimensional diffusion relaxation time (2D D-$T_2$) maps) may be obtained based on the acquisition of one or more signals generated by diffusion editing (DE) signals or sequences. These signals may be a modification of the Carr-Purcell-Meiboom-Gill (CPMG) signal where the first one or more echo spacings are systematically increased. As the initial echo spacings are increased in the presence of a gradient in the applied static field, the overall amplitudes of the subsequent echoes may be attenuated based on the diffusion coefficient (D) of the fluid. After the first one or more (e.g., two) echoes, the decay may be controlled by the transverse relaxation time $T_2$. By systematically varying the initial echo spacings, it may be possible to infer the D-$T_2$ map for the fluid.

The applied static and radiofrequency (RF) magnetic fields may be homogeneous or inhomogeneous. For inhomogeneous magnetic fields, the echo amplitudes may be described by Equation (1) below:

$$S(t_{E,L}, kt_E) = C \iint dT_2 dD\, f(D, T_2) k_{T2}(T_2, kt_E) k_D(D, b) \quad (1)$$

where S represents the measured echo amplitude, $t_{E,L}$ represents the initial echo spacing, k represents the echo number, $t_E$ represents the echo spacing during the subsequent CPMG train, C represents the amplitude calibration factor, $T_2$ represents the transverse relaxation time, D represents the diffusion coefficient, $f(D,T_2)$ represents the two-dimensional diffusion relaxation time distribution function, $k_{T2}$ represents the kernel for relaxation, $k_D$ represents the kernel for diffusion and b represents the diffusion sensitivity factor.

The kernel for relaxation $k_{T2}$ may be described by Equation (2):

$$k_{T2}(T_2,kt_E) = \exp\{-(n_{DE}t_{E,L}+kt_E)/T_2\} \quad (2)$$

where $n_{DE}$ represents the number of initial long echo spacings. For the typical case of $n_{DE}=2$, the kernel for diffusion $k_D$ may be described by Equations (3) and (4):

$$k_D = 1 \quad (3)$$

when $t_{E,L} = t_E$; and $$k_D = \alpha \exp\{-bD\} + \beta \exp\{-2bD\} \quad (4)$$

when the initial echo spacing $t_{E,L}$ differs from $t_E$. $\alpha$ represents the relative contributions of the direct echo pathway to the diffusion editing signal, and $\beta$ represents the relative contributions of the stimulated echo pathway to the diffusion editing signal.

For a given logging tool (e.g., LWD module 138 or 140), the diffusion sensitivity factor b may be determined by Equation (5):

$$b = \frac{1}{6}\gamma^2 g^2 t_{E,L}^3 \quad (5)$$

where $\gamma$ represents the gyromagnetic ratio, and g represents the gradient in the applied static field. When $t_{EL}=t_E$, the diffusion editing sequence becomes identical to the standard CPMG sequence.

The coefficients $\alpha$ and $\beta$ may be calibrated by placing a sample of fluid on the NMR logging tool (e.g., LWD module 138, 140). Equation (3) may apply when the initial echo spacing $t_{E,L}$ is substantially identical to the echo spacing during the subsequent CPMG train $t_E$. This may be the equivalent of the standard CPMG signal. In this case, the initial amplitude may be proportional to the calibration factor C. When the initial echo spacing is increased, Equation (4) shows that the signal of the DE signal may include two terms that are associated with the direct echo and stimulated echo coherence pathways during the initial two echo spacings. In this case, the initial signal decreases to C ($\alpha+\beta$). For the case when $n_{DE}=1$, Equations 3 and 4 may still apply, but with $\beta=0$ and b replaced by b/2.

Figure 2:
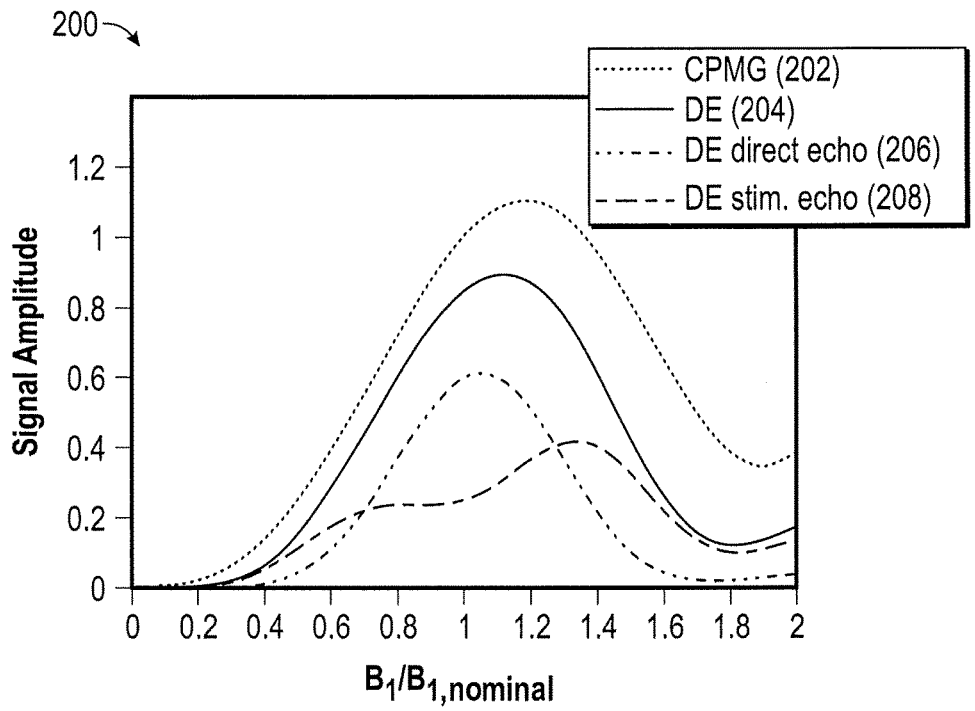
FIG. 2 depicts an illustrative graph showing a dependence of an initial signal strength as a function of the strength of an RF field, $B_1$, according to one or more embodiments disclosed.

FIG. 2 depicts an illustrative graph 200 showing the dependence of the initial signal strength as a function of the strength of the RF field, $B_1$, according to one or more embodiments disclosed. The X-axis represents the RF field $B_1$ normalized to its nominal value, and the Y-axis represents the signal amplitude. The initial echo amplitude of the DE signal when $t_{E,L}=t_E$ (identical to the CPMG signal) is shown as 202, and the DE signal when $t_{E,L}>t_E$ is shown as 204. The DE signal 204 may have two contributions: the direct echo shown as 206 and the stimulated echo shown as 208.

The calculation may assume a static field that is characterized by a substantially constant gradient perpendicular to the tool (e.g., LWD module 138, 140). This may lead to a thin sensitive region that extends along the tool. Within the sensitive region, the strength of the RF field may vary. For example, the RF field may be stronger and more uniform in the center and decay away from the center. The amplitude of the DE signal when $t_{E,L}=t_E$ may be larger than the amplitude of the DE signal when $t_{E,L}>t_E$, even in the absence of any diffusion. The ratio of the two initial amplitudes may be given by $\alpha+\beta$.

Figure 3:
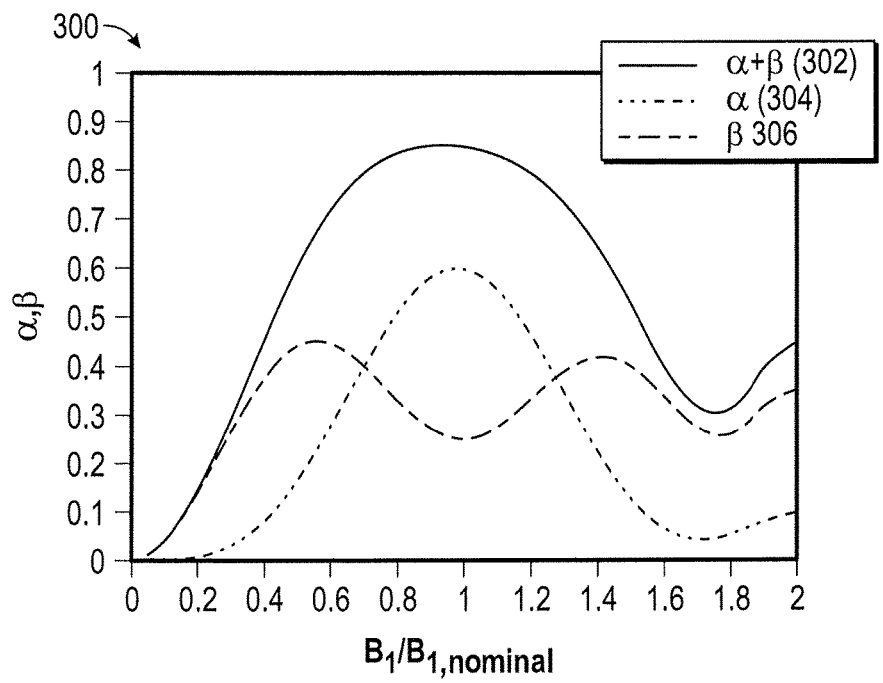
FIG. 3 depicts an illustrative graph showing a ratio of a diffusion editing amplitude to a CPMG amplitude as a function of the strength of the RF field, $B_1$ normalized to its nominal value, according to one or more embodiments disclosed.

FIG. 3 depicts an illustrative graph 300 showing a ratio 302 of the DE amplitude when $t_{E,L}>t_E$ to the DE amplitude when $t_{E,L}=t_E$ as a function of the strength of the RF field, $B_1$ normalized to its nominal value, according to one or more embodiments disclosed. This ratio 302 may correspond to $\alpha+\beta$ in Equation (2) above. The ratio $\alpha$ for the individual contribution associated with the direct echo pathway is shown as 304, and the ratio $\beta$ for the individual contribution associated with the stimulated echo coherence pathway is shown as 306. During a logging operation of a formation having a saturation that is inhomogeneous, or when the RF field strength deviates from its nominal value, the actual value of $\alpha+\beta$ may deviate from the value obtained from the calibration. A drop in $\alpha+\beta$ may sometimes be misinterpreted as the presence of fluids with high diffusion coefficients. A high diffusion coefficient may be $10^{-8}$ m$^2$/s or greater.

The coefficients $\alpha$ and $\beta$ may be determined by the distributions of the static field strength $B_0$ and the RF field strength $B_1$ across the sample of interest. For a given illustrative situation (e.g., logging tool, sample, and environmental conditions such as temperature, pressure, mud conductivity, saturation distribution, etc.), the relevant parameters may be summarized in a distribution function $F(\omega_0,\omega_1)$, where $\omega_0$ represents the offset to the local Larmor frequency from the RF frequency, and $\omega_1$ represents the local nutation frequency that is proportional to $B_1$. For any given set of $(\omega_0,\omega_1)$, $F(\omega_0,\omega_1)$ may be proportional to the number of spins that contribute to the signal at this particular offset frequency $\omega_0$ and nutation frequency $\omega_1$.

For spins that are characterized by the parameters ($\omega_0$, $\omega_1$), the contributions of the DE signal when $t_{E,L}=t_E$ is identical to the CPMG signal $C_{CPMG}(\omega_0,\omega_1)$ and may be divided into three contributions from the general DE signal: the direct echo contribution $C_{dir}(\omega_0,\omega_1)$, the stimulated echo contribution $C_{stim}(\omega_0,\omega_1)$, and the unfocused contributions $C_{unfoc}(\omega_0,\omega_1)$. As shown in Equation (6):

$$C_{CPMG}(\omega_0,\omega_1) = C_{dir}(\omega_0,\omega_1) + C_{stim}(\omega_0,\omega_1) + C_{unfoc}(\omega_0,\omega_1) \quad (6)$$

The third contribution $C_{unfoc}(\omega_0,\omega_1)$ may not lead to a detectable signal when the DE signal with $t_{E,L}>t_E$ is used.

The calibration factor may be given by Equation (7):

$$C = \iint d\omega_0 d\omega_1 F(\omega_0,\omega_1) c_{CPMG}(\omega_0,\omega_1) = \iint d\omega_0 d\omega_1 F(\omega_0,\omega_1)[c_{dir}(\omega_0,\omega_1) + c_{stim}(\omega_0,\omega_1) + c_{unfoc}(\omega_0,\omega_1)] \quad (7)$$

The diffusion kernel for the DE sequence when $t_{EL}>t_E$ may be given by Equation (8):

$$k_D(b,D) = [e^{-bD}\iint d\omega_0 d\omega_1 F(\omega_0,\omega_1) c_{dir}(\omega_0,\omega_1) + e^{-2bD}\iint d\omega_0 d\omega_1 F(\omega_0,\omega_1) c_{stim}(\omega_0,\omega_1)] C \quad (8)$$

From these equations, the coefficient $\alpha$ (i.e., the relative amplitude of the direct echo contribution to the DE signal) may be given by Equation (9):

$$\alpha = \frac{\iint d\omega_0 d\omega_1 F(\omega_0,\omega_1) c_{dir}(\omega_0,\omega_1)}{\iint d\omega_0 d\omega_1 F(\omega_0,\omega_1)\left[\begin{array}{c} c_{dir}(\omega_0,\omega_1) + \\ c_{stim}(\omega_0,\omega_1) + c_{unfoc}(\omega_0,\omega_1) \end{array}\right]} \quad (9)$$

Similarly, the coefficient β (i.e., the relative amplitude of the stimulated echo contribution to the DE signal) may be given by equation (10):

$$\beta = \frac{\int\int d\omega_0 d\omega_1 F(\omega_0, \omega_1) c_{stim}(\omega_0, \omega_1)}{\int\int d\omega_0 d\omega_1 F(\omega_0, \omega_1) \left[ \begin{array}{c} c_{dir}(\omega_0, \omega_1) + \\ c_{stim}(\omega_0, \omega_1) + c_{unfoc}(\omega_0, \omega_1) \end{array} \right]} \quad (10)$$

For a given NMR logging tool (e.g., LWD module 138, 140) and a uniform sample, these parameters may be determined experimentally. More particularly, these parameters may be used in the kernels of the inversion procedure that extracts the diffusion and relaxation properties from the measured data.

When the actual coefficients α and β deviate from the default values $\alpha_{default}$ and $\beta_{default}$, the D-T$_2$ maps may include artifacts. As used herein, the term "artifact" refers to contributions in the extracted distribution function that are present when inaccurate values of α and β are used. The artifacts may indicate that the inferred diffusion properties are inaccurate. The variations in α and β may be caused by modifications to $F(\omega_0, \omega_1)$. Modifications to $F(\omega_0, \omega_1)$ may be caused by a change in the quality factor Q, non-uniform saturation in the formation, or a combination thereof. The quality factor Q of the RF coil in the NMR tool (e.g., LWD module 138, 140) may change when the electrical conductivity of the formation changes. This may affect the amplitude of the RF pulses in the formation. A change in the quality factor Q may change $F(\omega_0, \omega_1)$. If Q is high, contributions from large offset frequencies may be filtered out so that they do not contribute to the detected signal. The contributions from large offset frequencies $\omega_0$ may be attenuated relative to the contributions close to resonance. This may affect both the CPMG signal and the DE signal, but the quantitative relative impact may not be identical. This may be seen from Equations (9) and (10).

Figure 4:
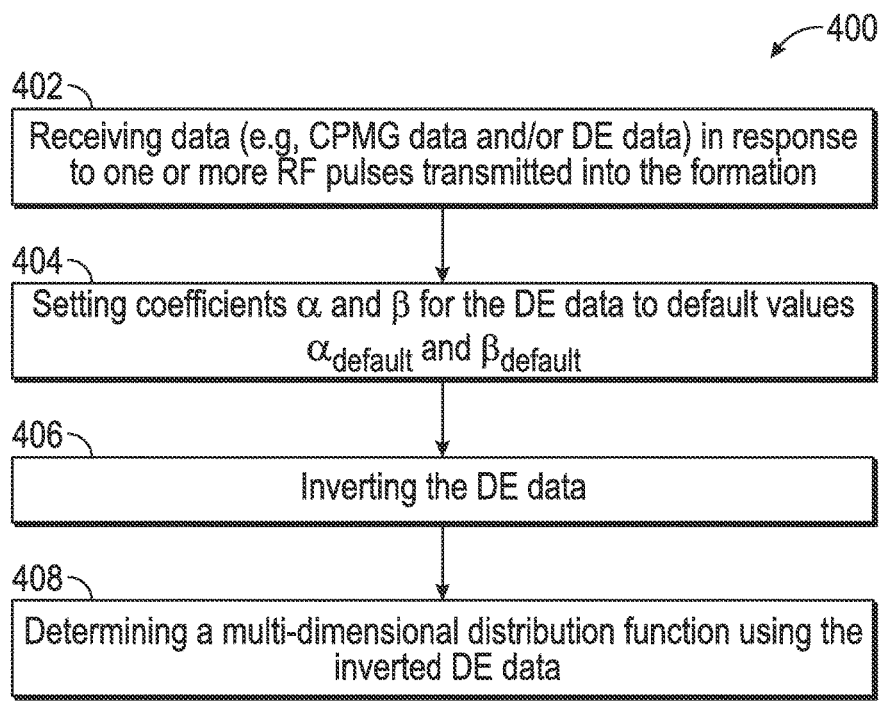
FIG. 4 depicts a flowchart of an illustrative method for generating a substantially artifact-free multi-dimensional distribution function, according to one or more embodiments disclosed.

FIG. 4 depicts a flowchart of an illustrative method 400 for generating a substantially artifact-free, multi-dimensional distribution function (e.g., a 2D D-T$_2$ map), according to one or more embodiments disclosed. Data may be received by the NMR logging tool (e.g., LWD module 138, 140 in FIG. 1) in response to one or more RF pulses transmitted into the formation by the NMR logging tool, as shown at 402. The data may include DE data with $t_{E,L}=t_E$ (identical to CPMG data), DE data with $t_{E,L}>t_E$, or a combination thereof. The coefficients α and β in the diffusion kernel for the DE data may be set to default values $\alpha_{default}$ and $\beta_{default}$ for the NMR logging tool, as shown at 404. For example, $\alpha_{default}$ may be from about 0.0 to about 1.0 or about 0.3 to about 1.0, and $\beta_{default}$ may be from about 0.0 to about 1.0 or about 0.0 to about 0.5.

The DE data with $t_{E,L}>t_E$ (excluding the CPMG data) may be inverted, as shown at 406. A multi-dimensional distribution function may be determined or extracted from the inverted DE data, as shown at 408. The distribution function may be 2D, 3D, or 4D, and the different dimensions may be the diffusion coefficient (D), the longitudinal relaxation time (T$_1$), the transverse relaxation time (T$_2$), a ratio of T$_1$/T$_2$, and/or depth of invasion (DOI). In at least one embodiment, the distribution function may be a D-T$_2$ distribution function.

For example, the DE data with $t_{E,L}>t_E$ may be fit to Equation (11):

$$S_{DE}(t_{E,L},kt_E) = \int\int dT_2 dD\, f_{fit}(D,T_2)[\alpha_{default}\exp\{-bD\} + \beta_{default}\exp\{-2bD\}]\exp\{-(2t_{E,L}+kt_E)/T_2\} \quad (11)$$

and the distribution function $f_{fit}(D,T_2)$ may be determined or extracted from Equation (11). The extracted distribution function $f_{fit}(D,T_2)$ may be free or substantially free from high diffusion artifacts that may otherwise appear at high diffusion coefficients with an inversion process including DE data with $t_{E,L}=t_E$ (CPMG data). The accuracy of the overall volumes of the inferred fluids may be improved by using the method shown below.

Figure 5:
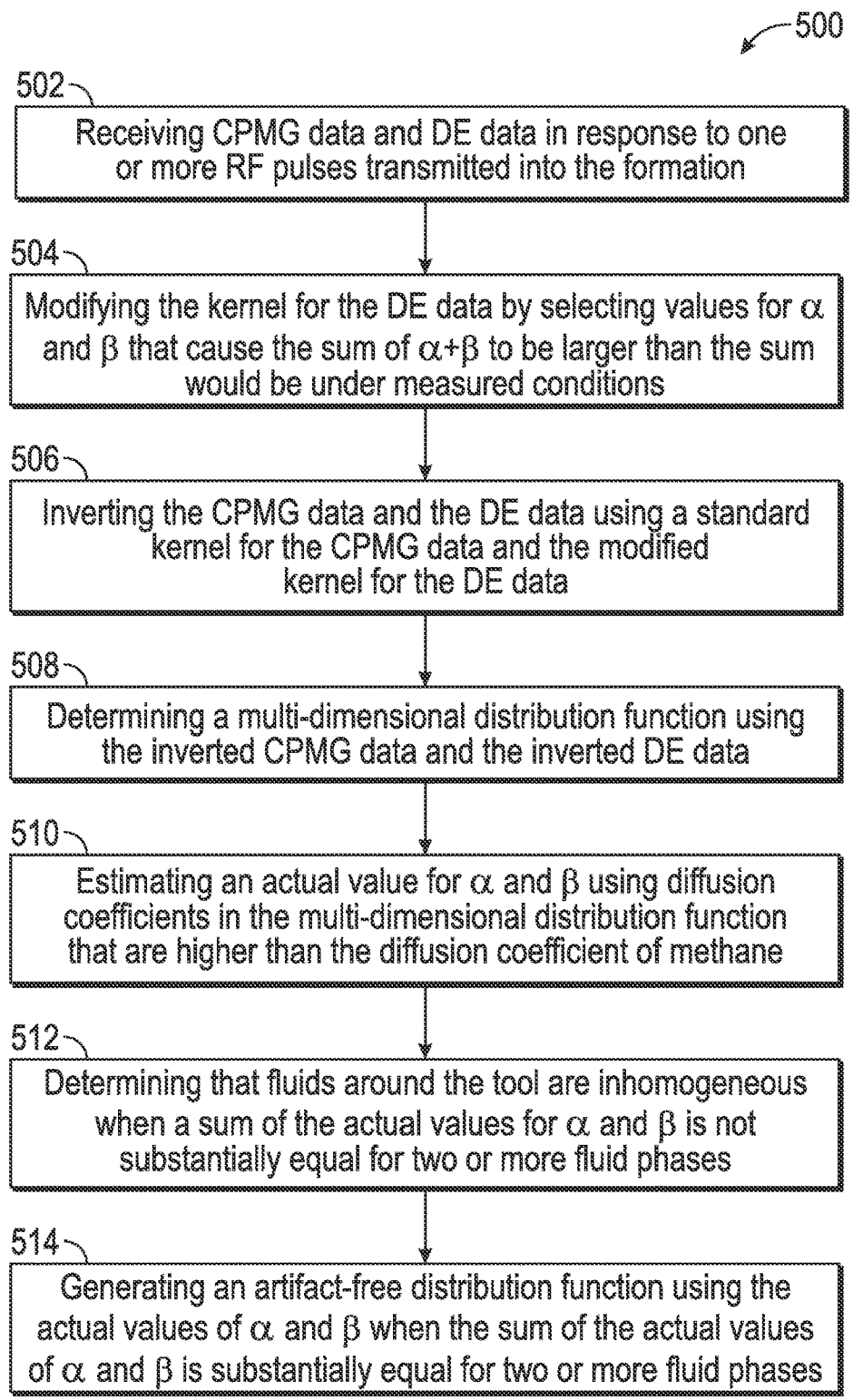
FIG. 5 depicts a flowchart of an illustrative method for identifying an artifact in a multi-dimensional distribution function, according to one or more embodiments disclosed.

FIG. 5 depicts a flowchart of an illustrative method 500 for identifying an artifact in a multi-dimensional distribution function (e.g., a 2D D-T$_2$ map), according to one or more embodiments disclosed. Data may be received by the NMR logging tool (e.g., LWD module 138, 140 in FIG. 1) in response to one or more RF pulses transmitted into the formation by the NMR logging tool, as shown at 502. The data may include DE data with $t_{E,L}=t_E$ (identical to CPMG data), DE data with $t_{E,L}>t_E$, or a combination thereof.

The kernel for the DE data with $t_{E,L}>t_E$ may be modified by selecting values for α and β that cause their sum (e.g., α+β) to be larger than the sum would be under any measured conditions, as shown at 504. The sum of α+β may be greater than or equal to about 0.8 or about 0.9. For example, the sum of α+β may be set to 1, and the ratio of α to β may be kept the same as the ratio of $\alpha_{default}$ to $\beta_{default}$. The DE data with $t_{E,L}=t_E$ (CPMG data) and the DE data with $t_{E,L}>t_E$ may be inverted using a standard kernel for the CMPG data and the modified diffusion kernel for the DE data with $t_{E,L}>t_E$, as shown at 506. As used herein, a "standard kernel" refers to Equation. 3.

A multi-dimensional distribution function may be determined or extracted from the inverted CMPG and the inverted DE data, as shown at 508. This distribution function may be 2D, 3D, or 4D, and the different dimensions may be the diffusion coefficient (D), the longitudinal relaxation time (T$_1$), the transverse relaxation time (T$_2$), a ratio of T$_1$/T$_2$, and/or depth of invasion (DOI). In at least one embodiment, the distribution function may be a D-T$_2$ distribution function. The distribution function may have a range of diffusion coefficients extending beyond the molecular diffusion coefficient of methane. The contributions of the distribution function at diffusion coefficients higher (e.g., at least 1.5 times higher) than the diffusion coefficient of methane may be quantified and together with the remainder of the distribution function may be used to infer or estimate the actual value of α and β for each fluid phase, as shown at 510. This information may then be used to infer or estimate whether the fluids are uniformly distributed in the formation and to calibrate the saturations.

For example, the CPMG (DE data with $t_{E,L}=t_E$) and DE data with $t_{E,L}>t_E$ may be fit to Equations (12) and (13) below:

$$S_{CPMG}(t_{E,L}=t_E, kt_E) = C\int\int dT_2 dD F_{raw}(D, T_2)^{-(2t_{E,L}+kt_E)/T_2} \quad (12)$$

$$S_{DE}(t_{E,L}, kt_E) = C\int\int dT_2 dD f_{raw}(D, T_2) \left(\left(\frac{1}{1+\frac{\beta_{default}}{\alpha_{default}}}\right)^{-bD} + \left(\frac{1}{1+\frac{\alpha_{default}}{\beta_{default}}}\right)^{-2bD}\right)^{-\frac{2t_{E,L}+kt_E}{T_2}} \quad (13)$$

The ratio $$\frac{\beta_{default}}{\alpha_{default}}$$

may be set to a default value (e.g., 0.2). The distribution function $f_{raw}(D,T_2)$ may then be determined or extracted from Equations (12) and (13).

Figure 6:
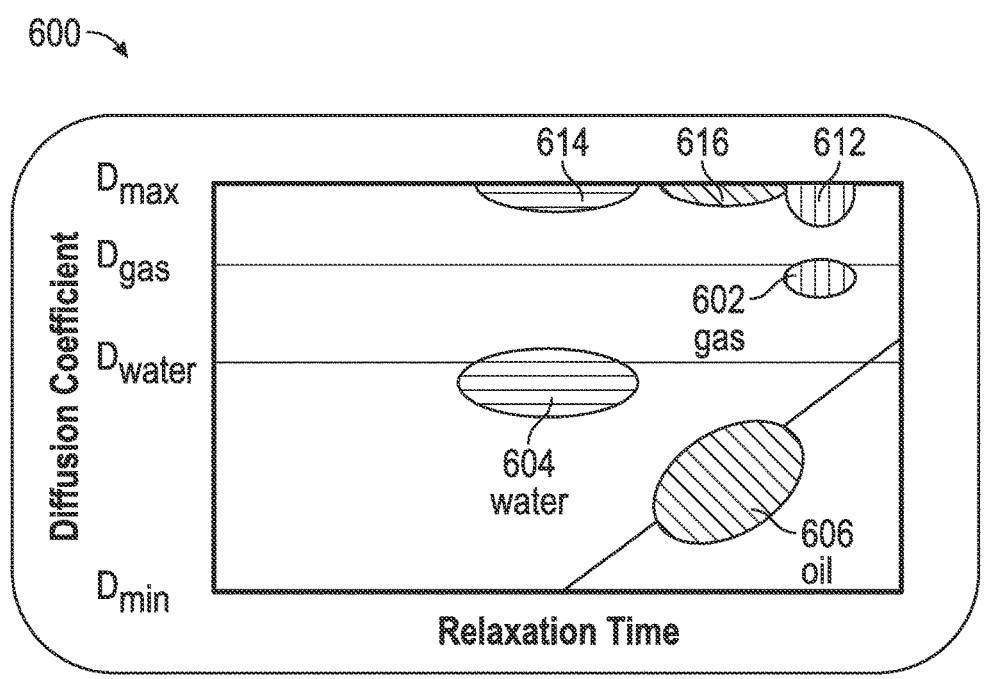
FIG. 6 depicts an illustrative graph showing the extracted distribution function $f_{raw}(D, T_2)$, according to one or more embodiments.

FIG. 6 depicts an illustrative graph 600 showing the extracted distribution function $f_{raw}(D,T_2)$, according to one or more embodiments. The X-axis represents the transverse relaxation time ($T_2$), and the Y-axis represents the diffusion coefficient (D). Gas is shown at 602, water is shown at 604, and oil is shown at 606. In addition to these contributions, there may be additional contributions 612, 614, 616 close to the maximum diffusion coefficient ($D_{max}$). These contributions 612, 614, 616 may be spurious signals caused by the true sum of $\alpha+\beta$ being different from the assumed value (e.g., 1). In at least one embodiment, $D_{max}$ may be larger than the gas diffusion coefficient ($D_{gas}$). For example, $D_{max}$ may be at least 2 times larger than $D_{gas}$.

Referring now to FIGS. 4 and 5, the actual value of $\alpha+\beta$ may be determined or extracted from $f_{raw}(D,T_2)$ for each fluid phase (e.g., gas 602, water 604, oil 606) by dividing the area of the contribution of a given fluid phase (e.g., water 604) by the total contribution for this fluid phase (e.g., 604+614). This may be represented mathematically by Equation (14):

$$(\alpha + \beta)(T_2) = \frac{\int_{D_{min}}^{D_{max}} dD\, f_{raw}(D, T_2)}{\int_{D_{gas}}^{D_{max}} dD\, f_{raw}(D, T_2)} \quad (14)$$

A determination may be made that the fluids are not uniformly distributed in the formation (i.e., the fluids are inhomogeneous) if the values of $\alpha+\beta$ are not equal or substantially equal for the different fluid phases, as shown at 512. If the values of $\alpha+\beta$ are equal or substantially equal for the different fluid phases (e.g., they differ by less than or equal to 0.05), but differ from the default values, then this new value of $\alpha+\beta$ may be used to generate an artifact free distribution function with improved saturation values, as shown at 514.

The method of FIGS. 4 and 5 may also be used to calibrate the sum of the coefficients $\alpha+\beta$ during the logging operation. For example, if we call the raw D-$T_2$ map by $f_{raw}(D,T_2)$, then the net value of $\alpha+\beta$ may be determined or extracted from Equation 15:

$$\langle \alpha + \beta \rangle = 1 - \frac{\int_{2D_{CH4}}^{D_{max}} dD \int_{T_{2,min}}^{T_{2,max}} dT_2 f_{raw}(D, T_2)}{\int_{2D_{min}}^{D_{max}} dD \int_{T_{2,min}}^{T_{2,max}} dT_2 f_{raw}(D, T_2)} \quad (15)$$

This value of $\alpha+\beta$ may be useful for quality assurance because the extracted value may be compared with the calibration value. Agreement between the extracted and calibrated values may indicate that no potential complication has arisen and that the default processing may be applied. In addition, this value of $\alpha+\beta$ may also improve calibration. For example, the extracted value may be used to replace the calibration value in the default processing. With this modified value, the default processing may avoid high diffusion artifacts.

If the saturation is not homogeneous in the sensitive region of the NMR logging tool (e.g., LWD module 138, 140), the relevant values of $\alpha+\beta$ may be different for the different fluid phases. This effect may be detected with a modification of the method described with respect to FIGS. 4 and 5. For example, using the raw extracted D-$T_2$ maps, the values of $\alpha+\beta$ may be estimated for one or more of the $T_2$ values separately, e.g., using Equation (16):

$$(\alpha + \beta)(T_2) = 1 - \frac{\int_{2D_{CH4}}^{D_{max}} dD\, f_{raw}(D, T_2)}{\int_{2D_{min}}^{D_{max}} dD\, f_{raw}(D, T_2)} \quad (16)$$

A homogeneous saturation may result in calculated values of $\alpha+\beta$ that are independent of $T_2$. However, if the extracted values from Equation (14) are different (e.g., by at least 0.05) at the different $T_2$ peaks of the relaxation time distribution, then the saturation may be inhomogeneous. An inhomogeneous saturation may be caused by non-uniform invasion. As used herein, the term "invasion" refers to fluid from the wellbore replacing fluid in the earth formation. When this analysis is performed for different depths of invasion, it may be determined how deep the non-uniform invasions reach. This may also affect the response of other logging tools (e.g., electrical conductivity tools). Knowledge of this condition may avoid misinterpretation of data acquired by such tools.

Figure 7:
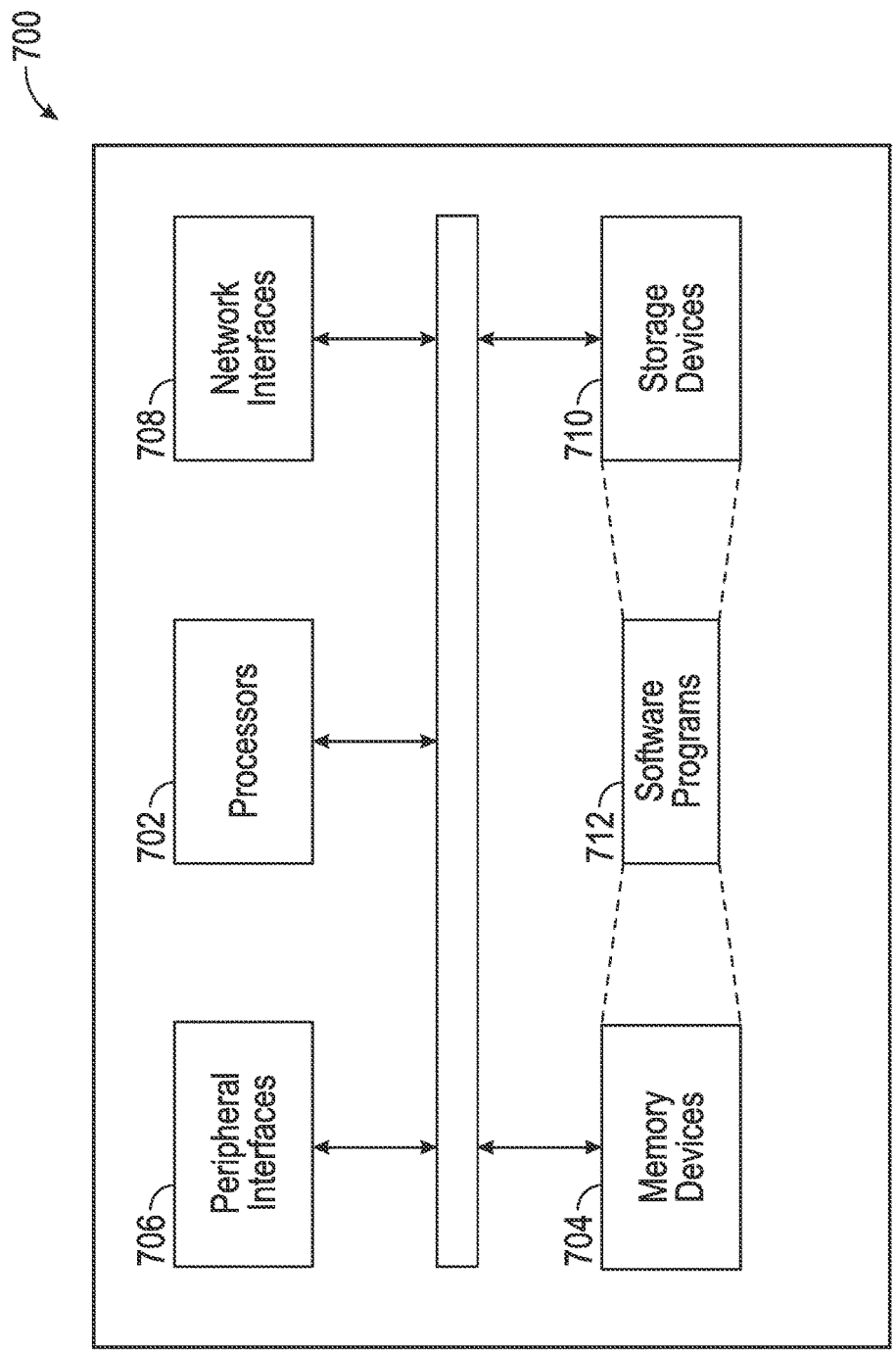
FIG. 7 depicts an illustrative schematic view of a computing or processor system capable of performing at least a portion of one or more of the methods disclosed herein, according to one or more embodiments disclosed.

Embodiments of the disclosure may also include one or more computing or processor systems for implementing one or more embodiments of the methods 400, 500. FIG. 7 illustrates a schematic view of such a computing or processor system 700, according one or more embodiments disclosed. Embodiments of the NMR logging tool (e.g., LWD module 138, 140) may be or include embodiments of the processor system 700. In other embodiments, the processor system 700 may be remotely connected to one or more components of the LWD module 138, 140.

The processor system 700 may include one or more processors 702 of varying core configurations (including multiple cores) and clock frequencies. The one or more processors 702 may be operable to execute instructions, apply logic, etc. It will be appreciated that these functions may be provided by multiple processors or multiple cores on a single chip operating in parallel and/or communicably linked together. In at least one embodiment, the one or more processors 702 may be or include one or more GPUs.

The processor system 700 may also include a memory system, which may be or include one or more memory devices and/or computer-readable media 704 of varying physical dimensions, accessibility, storage capacities, etc. such as flash drives, hard drives, disks, random access memory, etc., for storing data, such as images, files, and program instructions for execution by the processor 702. In an embodiment, the computer-readable media 704 may store instructions that, when executed by the processor 702, are configured to cause the processor system 700 to perform operations. For example, execution of such instructions may cause the processor system 700 to implement one or more portions and/or embodiments of the method(s) described above.

The processor system 700 may also include one or more network interfaces 706. The network interfaces 706 may include any hardware, applications, and/or other software. Accordingly, the network interfaces 706 may include Ethernet adapters, wireless transceivers, PCI interfaces, and/or serial network components, for communicating over wired or wireless media using protocols, such as Ethernet, wireless Ethernet, etc.

As an example, the processor system 700 may be a mobile device that includes one or more network interfaces for communication of information. For example, a mobile device may include a wireless network interface (e.g., operable via one or more IEEE 802.11 protocols, ETSI GSM, BLUETOOTH®, satellite, etc.). As an example, a mobile device may include components such as a main processor, memory, a display, display graphics circuitry (e.g., optionally including touch and gesture circuitry), a SIM slot, audio/video circuitry, motion processing circuitry (e.g., accelerometer, gyroscope), wireless LAN circuitry, smart card circuitry, transmitter circuitry, GPS circuitry, and a battery. As an example, a mobile device may be configured as a cell phone, a tablet, etc. As an example, a method may be implemented (e.g., wholly or in part) using a mobile device. As an example, a system may include one or more mobile devices.

The processor system 700 may further include one or more peripheral interfaces 708, for communication with a display screen, projector, keyboards, mice, touchpads, sensors, other types of input and/or output peripherals, and/or the like. In some implementations, the components of processor system 700 need not be enclosed within a single enclosure or even located in close proximity to one another, but in other implementations, the components and/or others may be provided in a single enclosure. As an example, a system may be a distributed environment, for example, a so-called "cloud" environment where various devices, components, etc. interact for purposes of data storage, communications, computing, etc. As an example, a method may be implemented in a distributed environment (e.g., wholly or in part as a cloud-based service).

As an example, information may be input from a display (e.g., a touchscreen), output to a display or both. As an example, information may be output to a projector, a laser device, a printer, etc. such that the information may be viewed. As an example, information may be output stereographically or holographically. As to a printer, consider a 2D or a 3D printer. As an example, a 3D printer may include one or more substances that can be output to construct a 3D object. For example, data may be provided to a 3D printer to construct a 3D representation of a subterranean formation. As an example, layers may be constructed in 3D (e.g., horizons, etc.), geobodies constructed in 3D, etc. As an example, holes, fractures, etc., may be constructed in 3D (e.g., as positive structures, as negative structures, etc.).

The memory device 704 may be physically or logically arranged or configured to store data on one or more storage devices 710. The storage device 710 may include one or more file systems or databases in any suitable format. The storage device 710 may also include one or more software programs 712, which may contain interpretable or executable instructions for performing one or more of the disclosed processes. When requested by the processor 702, one or more of the software programs 712, or a portion thereof, may be loaded from the storage devices 710 to the memory devices 704 for execution by the processor 702.

Those skilled in the art will appreciate that the above-described componentry is merely one example of a hardware configuration, as the processor system 700 may include any type of hardware components, including any necessary accompanying firmware or software, for performing the disclosed implementations. The processor system 700 may also be implemented in part or in whole by electronic circuit components or processors, such as application-specific integrated circuits (ASICs) or field-programmable gate arrays (FPGAs).

While the specific embodiments described above have been shown by way of example, it will be appreciated that many modifications and other embodiments will come to the mind of one skilled in the art having the benefit of the teachings presented in the foregoing description and the associated drawings. Accordingly, it is understood that various modifications and embodiments are intended to be included within the scope of the appended claims.

What is claimed is:

1. A method for generating a multi-dimensional distribution function, comprising:
   receiving first data and second data in response to one or more radiofrequency pulses that are transmitted into a subterranean formation, wherein the first data comprises Carr-Purcell-Meiboom-Gill data, and the second data comprises diffusion editing data with initial echo spacings longer than subsequent echo spacings;
   inverting the second data;
   determining, using a processor, a multi-dimensional distribution function using the inverted second data;
   determining a sum of $\alpha+\beta$ for a first fluid phase and a sum of $\alpha+\beta$ for a second fluid phase based at least in part on the multi-dimensional distribution function, wherein $\alpha$ represents a relative contribution of a direct echo pathway and $\beta$ represents a relative contribution of a stimulated echo pathway; and
   applying an updated value of $\alpha$ and $\beta$ to the multi-dimensional distribution function when the sum of $\alpha+\beta$ for the first fluid phase is equal to the sum of $\alpha+\beta$ for the second fluid phase to remove one or more artifacts.

2. The method of claim 1, wherein the first data is not inverted.

3. The method of claim 1, wherein the multi-dimensional distribution function comprises a two-dimensional distribution function.

4. The method of claim 1, wherein the multi-dimensional distribution function comprises a three-dimensional distribution function or a four-dimensional distribution function.

5. The method of claim 1, wherein one or more dimensions of the multi-dimensional distribution function are selected from the group consisting of: a diffusion coefficient, a longitudinal relaxation time, a transverse relaxation time, and a depth of invasion.

6. The method of claim 1, further comprising selecting default values for $\alpha$ and $\beta$ in a diffusion kernel of the second data.

7. The method of claim 1, wherein the default value for $\alpha$ is from 0.3 to 1.0, and wherein the default value for $\beta$ is from 0.0 to 0.5.

8. A method for identifying an artifact in a multi-dimensional distribution function, comprising:
   receiving first data and second data in response to one or more radiofrequency pulses that are transmitted into a subterranean formation, wherein the first data comprises Carr-Purcell-Meiboom-Gill data, and the second data comprises diffusion editing data with initial echo spacings longer than subsequent echo spacings;
   modifying a kernel for the second data by selecting values for $\alpha$ and $\beta$ that cause a sum of $\alpha+\beta$ to be larger than the sum would be under measured conditions, wherein α represents a relative contribution of a direct echo pathway to the second data, and wherein β represents a relative contribution of a stimulated echo pathway to the second data;

inverting the first data and the second data using the modified kernel for the second data;

determining, using a processor, a multi-dimensional distribution function using the inverted first data and the inverted second data;

determining a sum of α+β for a first fluid phase and a sum of α+β for a second fluid based at least in part on the multi-dimensional distribution function and a diffusion coefficient that is higher than a diffusion coefficient of methane; and determining a depth of a non-uniform invasion when the sum of α+β for the first fluid phase is not substantially equal to the sum of α+β for the second fluid phase.

9. The method of claim 8, wherein the selected values for α and β cause the sum of α+β to be greater than or equal to 0.9.

10. The method of claim 8, wherein inverting the first data and the second data comprises using a standard kernel for the first data.

11. The method of claim 8, wherein the multi-dimensional distribution function comprises a two-dimensional distribution function, a three-dimensional distribution function, or a four-dimensional distribution function.

12. The method of claim 8, wherein one or more dimensions of the multi-dimensional distribution function are selected from the group consisting of: a diffusion coefficient, a longitudinal relaxation time, a transverse relaxation time, and a depth of invasion.

13. The method of claim 8, further comprising generating a second multidimensional distribution function when a sum of the actual values for α and β for a first fluid phase are substantially equal to a sum of the actual values for α and β for a second fluid phase, and wherein the second multi-dimensional distribution function is substantially artifact-free.

14. A computing system, comprising:
one or more processors; and
a non-transitory computer-readable media storing instructions thereon that, when executed by at least one of the one or more processors, cause the computing system to perform operations, the operations comprising:
receiving first data and second data in response to one or more radiofrequency pulses that are transmitted into a subterranean formation, wherein the first data comprises Carr-Purcell-Meiboom-Gill data, and the second data comprises diffusion editing data with initial echo spacings longer than subsequent echo spacings;
inverting the second data;
determining a multi-dimensional distribution function using the inverted second data;
determining a sum of α+β for a first fluid phase and a sum of α+β for a second fluid based at least in part on the multi-dimensional distribution function and a diffusion coefficient that is higher than a diffusion coefficient of methane; and
determining a depth of a non-uniform invasion when the sum of α+β for the first fluid phase is not substantially equal to the sum of α+β for the second fluid phase.

15. The computing system of claim 14, wherein determining the multi-dimensional distribution function using the inverted second data removes an artifact in a diffusion dimension of the multi-dimensional distribution function, and wherein one or more dimensions of the multi-dimensional distribution function are selected from the group consisting of: a diffusion coefficient, a longitudinal relaxation time, a transverse relaxation time, and a depth of invasion.

* * * * *